United States Patent [19]
Clement

[11] Patent Number: 5,403,268
[45] Date of Patent: Apr. 4, 1995

[54] ARM SUPPORT

[75] Inventor: Richard Clement, Groton, Mass.

[73] Assignee: Med-Techna, Inc., Dedham, Mass.

[21] Appl. No.: 142,216

[22] Filed: Oct. 25, 1993

[51] Int. Cl.6 .............................................. A61F 5/00
[52] U.S. Cl. ........................................ 602/20; 602/4; 128/DIG. 19
[58] Field of Search ............... 602/4, 5, 12, 19, 20, 602/53, 60–62; 128/DIG. 19; 2/44, 45, 92

[56] References Cited

U.S. PATENT DOCUMENTS

| | | |
|---|---|---|
| 2,425,288 | 2/1947 | Jordan . |
| 3,103,216 | 9/1963 | Scott . |
| 3,404,680 | 10/1968 | Guttman et al. . |
| 3,433,221 | 3/1969 | Kendall et al. . |
| 3,548,818 | 12/1970 | Kaplan . |
| 3,906,944 | 9/1975 | Christen . |
| 4,188,944 | 2/1980 | Augustyalak . |
| 4,198,964 | 4/1980 | Honneffer . |
| 4,437,459 | 3/1984 | Slavetskas . |
| 4,446,858 | 5/1984 | Verter .............................. 602/4 |
| 4,446,859 | 5/1984 | Pedersen . |
| 4,476,859 | 10/1984 | Kloepfer et al. . |
| 4,598,703 | 7/1986 | Lindemann ...................... 602/4 |
| 4,735,198 | 4/1988 | Sawa ................................ 2/44 X |
| 4,784,128 | 11/1988 | Scheuermann . |
| 4,905,713 | 3/1990 | Moranta . |
| 4,986,266 | 1/1991 | Lindemann . |
| 5,188,587 | 2/1993 | McGuire et al. ................ 602/20 |

FOREIGN PATENT DOCUMENTS

1147711 4/1963 Germany .

OTHER PUBLICATIONS

"Harnessing and Controls for Body-Powered Devices", p. 135 and p. 145 (prior to 1990).

Primary Examiner—Richard J. Apley
Assistant Examiner—Linda C. M. Dvorak
Attorney, Agent, or Firm—Wolf, Greenfield & Sacks

[57] ABSTRACT

An arm support comprises a shoulder saddle and an arm cuff for suspending the arm with a plurality of suspension straps extending between the cuff and saddle for unloading the weight of the arm from the shoulder joint while the plurality of straps permit a wide range of motion of the shoulder joint and positive support for the arm.

11 Claims, 3 Drawing Sheets

ARM SUPPORT

BACKGROUND OF THE INVENTION

There are many slings or brace-type apparatus in the prior art for supporting and immobilizing an arm of an individual. The known prior art devices vary from a simple sling arrangement where the lower arm is supported in sling-like fashion by bands passing to an opposite shoulder of the arm being supported, to more complex arm supports that attempt to support the arm through upper arm contact with devices having interconnection with shoulder support means in various arrangements and configurations. In many cases, such devices can be awkward to use, heavy, non-fully supportive because of slippage of the arm with respect to the shoulder or have other undesirable characteristics.

SUMMARY OF THE INVENTION

An object of this invention is to provide an arm support which is designed to reduce forces acting to, sublux the shoulder-arm joint, yet allow a wide or free range of motion to all of the arm segments.

Still another object of this invention is to provide an arm support which has sufficient adjustability to provide for various stages of rehabilitation of the arm and comfort and suspension and adjustability during any of such stages, including adjustability of the arm with respect to the shoulder.

Still another object of the invention is to provide an arm support for positively holding and supporting the arm without the use of a supplemental arm sling or other arm load relieving device.

According to the invention, an arm support for suspending the arm of a user below the user's shoulder joint has a shoulder saddle acting as a base for the support. An upper arm cuff preferably has a high friction inner surface for contact directly with the arm or indirectly therewith through an arm covering of the user. A plurality of adjustment straps extend between the shoulder saddle and the arm cuff for unloading the weight of the arm from the shoulder joint. Preferably, the straps are three in number and allow for a full range of positioning of the arm cuff with respect to the shoulder saddle. Thus the straps provide for the humeral head to be pulled toward the glenoid fossa of the scapula. The straps and arm cuff as a whole act in a manner similar to the deltoids to maintain the integrity of the shoulder.

Preferably the straps have a VELCRO-type or releasable attachment to one of the cuff or shoulder saddle to increase adjustability and desired positioning of the straps. This attachment of each strap can be made at any desired location on the cuff.

The arm cuff provides an inner surface having a high coefficient of friction which acts directly on the arm or indirectly through a covering of the arm to prevent the arm from slipping with respect to the cuff. The cuff can carry an adjustable biceps-triceps belly component to positively lock the cuff in place and aid in preventing the arm from slipping with respect to the cuff.

It is a feature of this invention that the arm support can be made of lightweight materials having sufficient strength to fully support the arm with minimized discomfort to the body of an individual. Full adjustability of the arm with respect to the shoulder can be obtained and the need for supplementary sling can be avoided. The arm support is so formed that it is highly versatile and a single size will adjust and adapt to a wide variety of individual sizes reducing stocking requirements for sellers and distributors.

Lack of muscle tone about a shoulder joint of an individual following peripheral nerve injury or other trauma can cause painful subluxation. The arm support of this invention reduces forces acting to sublux the joint at the shoulder while allowing a free range of motion of all arm segments and provides for adjustability during various stages of rehabilitation.

The weight of the arm alone is enough to force stretching of the ligaments of the shoulder when no coordinating muscle activity is present. Conventional slings are the normal avenues of approach but they are limited with respect to adjustability, comfort and stability. The improved slings of this invention incorporate orthopedic principles to provide reliable adjustable configurations with positive support by the shoulder saddle and a cuff which is preferably a humeral cuff around the humerus of the individual. The arm support does not immobilize or limit motion which is an important key to proper treatment of a painful shoulder. If the shoulder is immobilized, the shoulder can cause contractions and increased pain.

BRIEF DESCRIPTION OF THE DRAWINGS

The above and other features, advantages and objects of this invention will be better understood from a reading of the following specification in conjunction with the accompanying drawings in which.

BRIEF DESCRIPTION OF THE INVENTION

Figure 1:
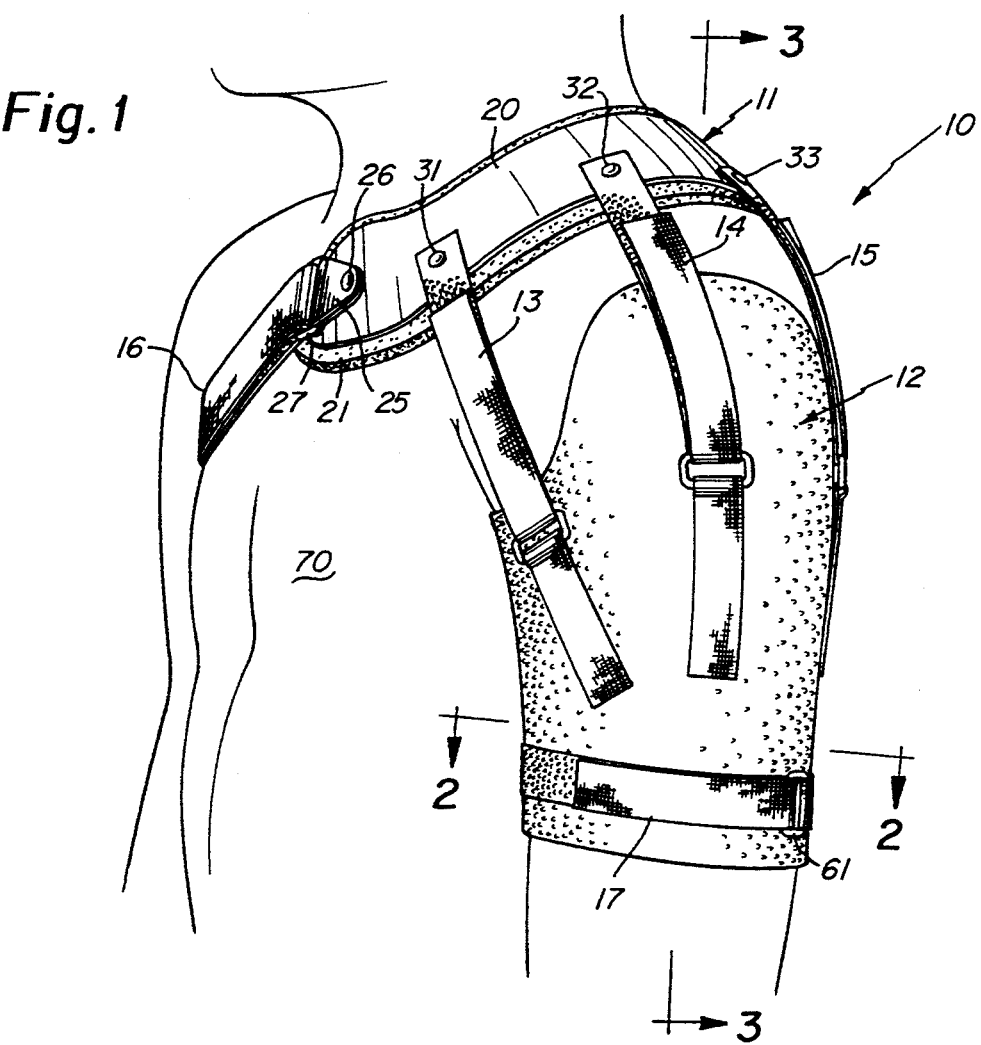
FIG. 1 is a left perspective view of a preferred embodiment of the arm support of this invention supporting the left arm of a human.

With reference now to the drawings, a preferred embodiment of an arm support 10 is shown in FIG. 1 having a shoulder saddle 11 acting as a base for an arm cuff 12 attached to the saddle by a plurality of suspension support straps or bands 13, 14 and 15. The shoulder saddle 11 is fixed in place on an individual partially at 70 by a shoulder strap 16 while a biceps-triceps strap 17 acts to provide positive support for the arm within the cuff 12 aiding in preventing slipping of the arm with respect to the cuff.

The shoulder saddle 11 acts as a base for the entire arm support. The saddle 11 is preferably formed of a stiff yet flexible piece of material in the form of a thin band or strip 20 as for example having a length of 18 inches, a width of 3 inches, and a thickness of 1/16 inch. The strip 20 is preferably adhered to an underlying padding 21 which can be formed of a sponge rubber or polymeric material roughly conforming to the shape of the strip 20 but extending out beyond its edges to provide full padding.

The particular materials of the strip 20 and padding 21 can vary greatly. Various polymeric materials can be used and in some cases cloth can be used for the padding, while metal or other materials can be used for the stiff yet resilient strip 20.

The shoulder saddle extends from the chest of an individual over the shoulder to the back thereof providing for positive support. It is held in place by a strap or band 16, best shown in FIG. 4, attached to one end of the saddle by rivet 24. The other end of the saddle 11 carries a mounting tab 25 riveted at 26 to the saddle. The tab 25 has a D plastic or metal ring or member 27 which receives the end 28 of the strap 16. The strap 16 has a VELCRO (a trademarked product of VELCRO Inc. of New Hampshire) attachment in the preferred embodiment with loop materials and hook materials as shown at 29 and 30 as known in the art. Thus, the strap is fully adjustable by pulling the end 28 through the D and tightening as desired after which the looped and hooked VELCRO materials are engaged to determine the length of the strap 16 and to mount the shoulder harness on the individual. In a preferred embodiment, elements 29 and 30 can be VELCRO hooks and a separate tab having hooks on either side can be used to form the engagement of the end 28 on itself to position the saddle 11 in place.

The specific materials of the strap 16 can vary greatly. Cloth, conventional textile tape, polymeric materials and the like can be used. It is preferred that the rivets allow for pivotal movement at 24 and 26 giving further adjustability to the mounting and adjustment of the saddle.

Figure 3:
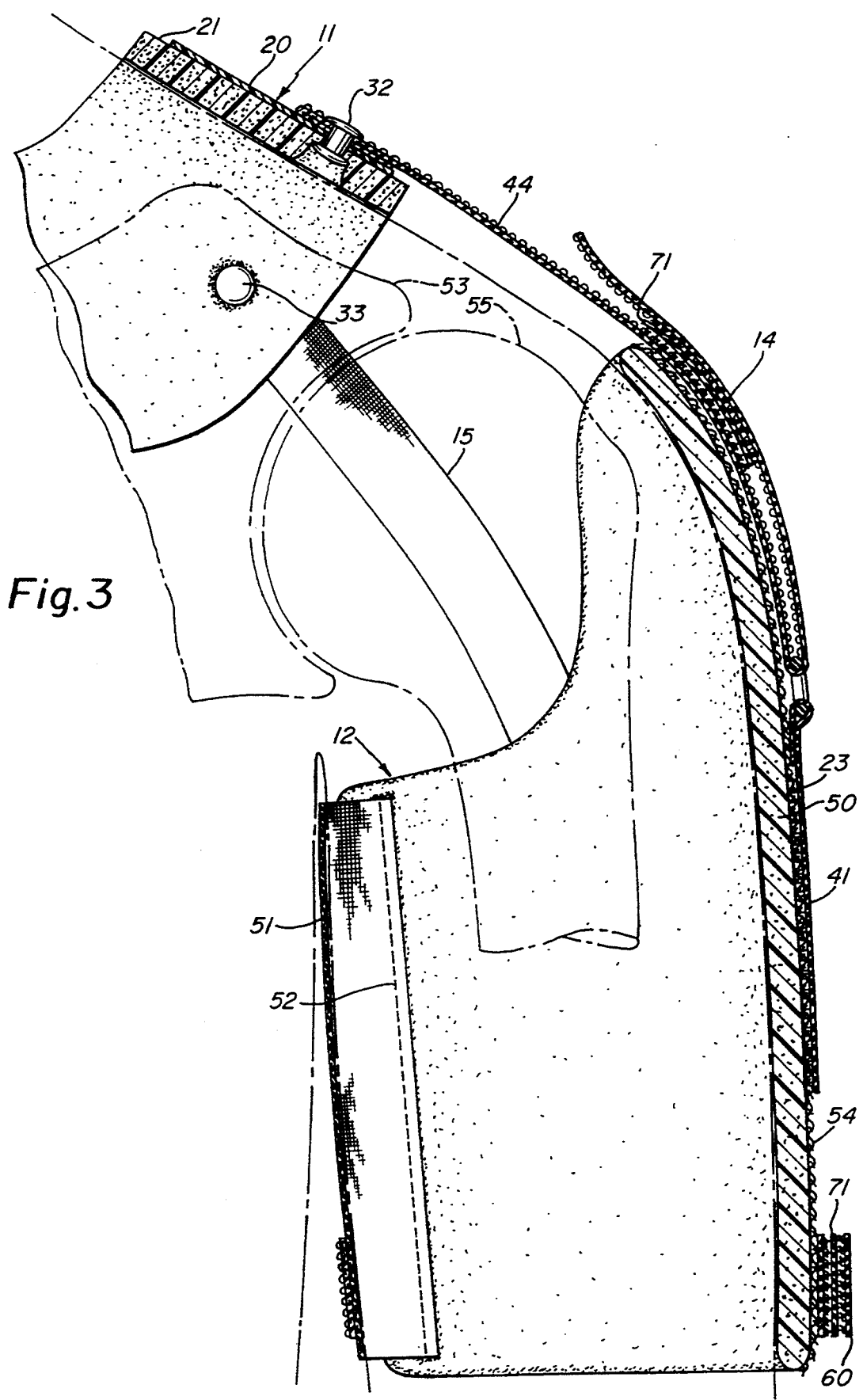
FIG. 3 is a cross sectional view thereof taken through line 3—3 of FIG. 1.
Figure 4:
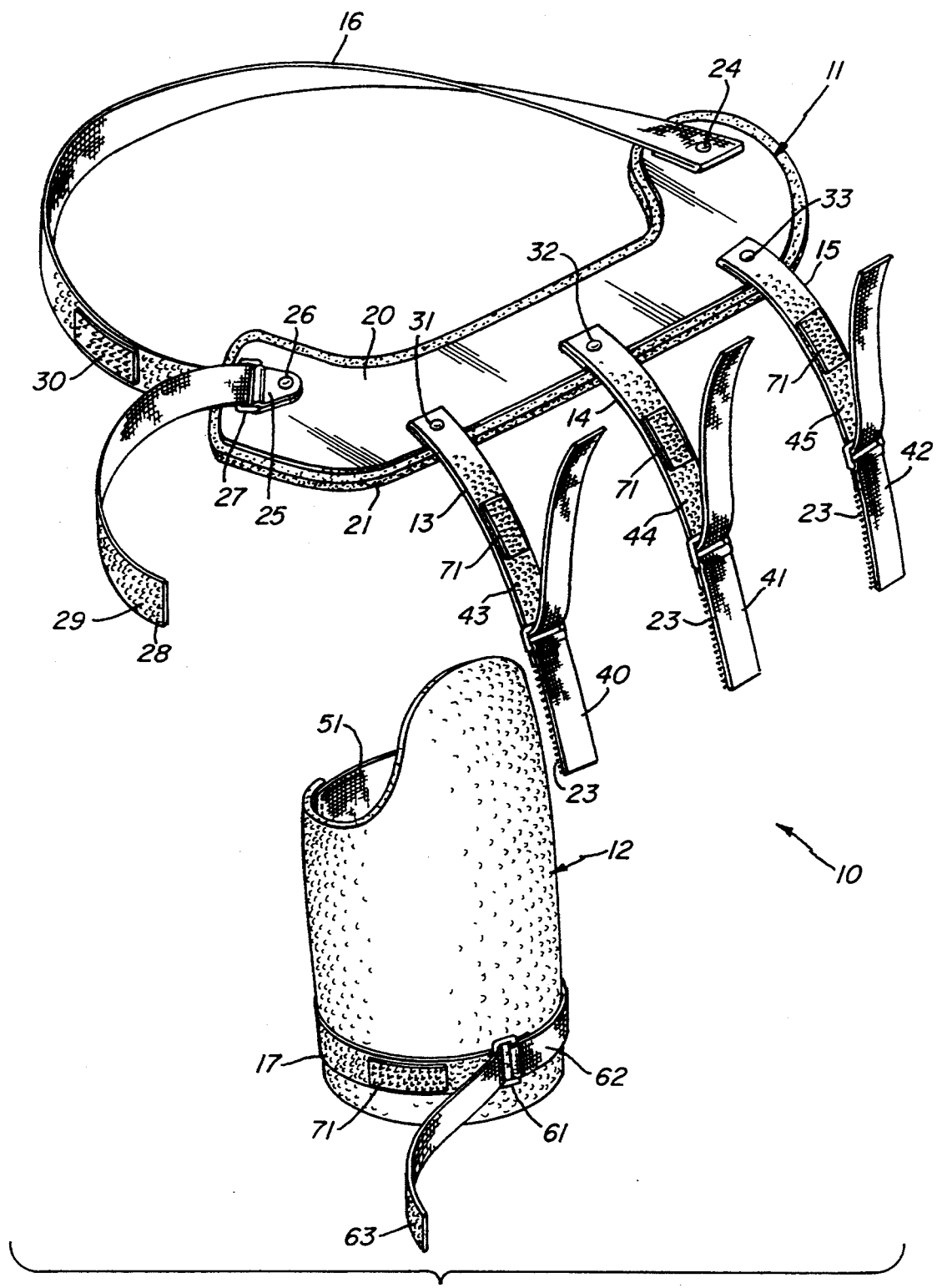
FIG. 4 is an exploded view in perspective illustrating the various components of the arm support of the preferred embodiment of this invention.

Rivets 31, 32 and 33 mount the upper ends of the bands or straps 13, 14 and 15 as shown in FIG. 4. Preferably each strap 13, 14 and 15 are identical although this is not required, and each strap comprises a VELCRO hook portion as shown at 23 attached to a D ring mounting strap 40, 41 and 42 forming a part of the overall supporting straps. The strap portions 40, 41 and 42 carry VELCRO hooks at 23 to allow attachment at various desired points on the humeral cuff 12 as will be described. Total adjustability is achieved by VELCRO mounting as well as the use of a D ring at the end of each strap portion 40, 41 and 42. Suitable loop materials shown on portions 43, 44 and 45 of the bands 13, 14 and 15 allow locking in place substantially in the same manner as described with respect to band 23 to allow full adjustability of the cuff 12 and the shoulder saddle 11. Note portions 43, 44, 45 require use of a double sided VELCRO type hook strip 71 to form the connection shown in FIG. 3. In some cases, the strip 71 can be eliminated and loop and lock material provided directly on back portions 43, 44 and 45.

In the preferred embodiment, the arm cuff which overlies the humerus encircles the arm and has a first non-slip resilient foam lining 50 covering approximately 270° of the circumference of the arm with an elastic band 51 stitched to the foam at 52 covering the remainder of the circumference of the arm. The elastic band and non-slip foam lining provide for good attachment to the arm or a covering such as a shirt over the arm. There is a high friction surface in the foam lining that prevents the arm or its covering from substantially slipping with respect to the cuff and thereby act to fully support the arm against dropping and sliding through the cuff. The cuff is, of course, selected sized to provide a resilient frictional fit with the arm preferably about the humerus 52 of the arm thereby maintaining the humerus in proper position with respect to the scapula 53 at the shoulder joint as best shown in FIG. 3. In the preferred embodiment, the foam is a polyurethane foam having a density of 1–2 lbs/cu. ft. and can be obtained from VELCRO, Inc. of New Hampshire.

The cuff portion 50 preferably has a surrounding VELCRO type looped outside material 54 which provides a base to enable attachment of the ends 40, 41, 42 on any portion of the cuff desired to provide proper positioning of the arm with respect to the scapula.

As a further component for preventing the arm from moving with respect to the cuff, a biceps-triceps band 17 is provided having a D fastener 61 at one end 62 of a strip heat sealed at 70 to the adjustment end of band 17 with VELCRO loops 63 at the other end. This allows adjustment of the band 17 preferably below the bulge of the arm muscle at the humerus to again provide positive support once the straps 13, 14 and 15 are positioned. If desired, hooks can be provided on an undersurface of the band 17 so that the band 60 is positively positioned with respect to the arm cuff by engaging the looped surface thereof. A double-sided mounting or adjustment strip 71 has VELCRO hoops on either side to enable adjustment of band 17.

In use, the arm support, sometimes called a hemisling is attached as shown in FIGS. 1 and 3 to the body of a user. Each of the straps 13, 14 and 15 is adjusted to provide for proper distancing of the cuff from the shoulder saddle. The position of the arm with respect to the shoulder about the circumference of the arm is also adjusted by proper positioning as desired of the straps 13, 14 and 15. Thus the straps provide both a distancing of the arm from the shoulder and also a rotational positioning of the arm with respect to the shoulder.

Figure 2:
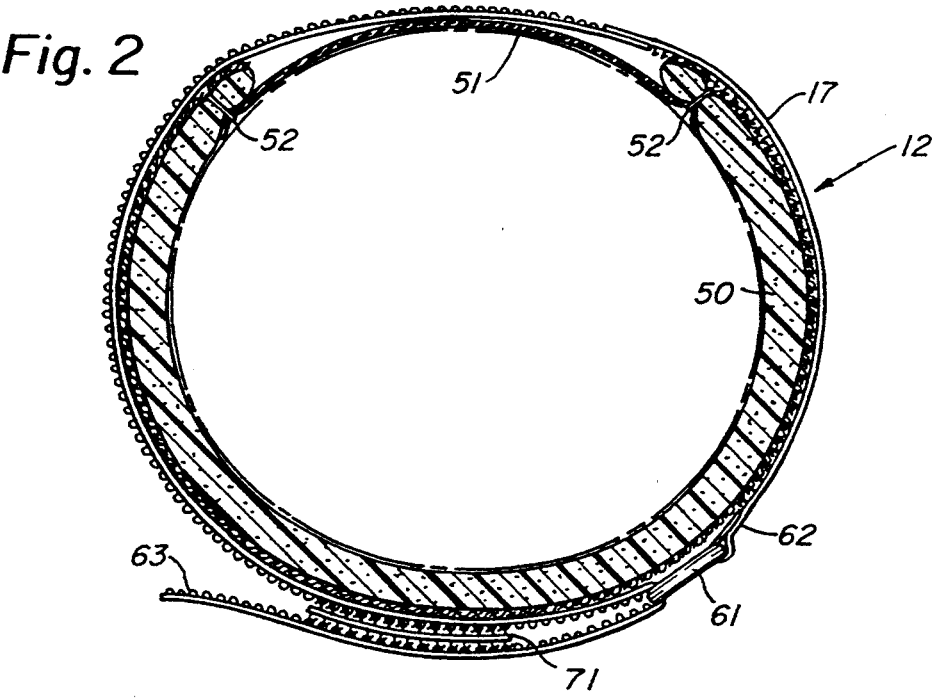
FIG. 2 is a cross sectional view thereof taken through line 2—2 thereof.

FIG. 2 more clearly shows the strap or band 17 as a two-part piece heat sealed at 70 to provide ease of manufacture with hooks on one portion going to the D ring and loops on the other portion going to the end. The double hook strap 71 is provided to make the joint between portions of the strap after the strip end passes through the D ring. Such a construction can be the same as used in each of the straps 13, 14 and 15, as for example shown in FIG. 3, with strap 14.

In the preferred embodiment, the humeral cuff has a non-slip foam lining portion 50 of polyurethane foam having a thickness of $\frac{3}{10}$ inch and an overall top to bottom cuff length of 9 inches with an inner diameter when unstretched of approximately 4 inches (depending on arm size). The bands 13, 14 and 15 preferably have a width of 1 inch, and are formed of VELCRO type hook and loop material. The band size can change with arm size. The bands provide for adjustability of approximately 6 inches to $\frac{1}{2}$ inch between the cuff and the shoulder saddle but depend on the arm size.

While a specific embodiment of this invention has been shown and described, it should be understood that many variations are possible. For example, specific materials can vary greatly. Additionally, while VELCRO attachments and adjustments are preferred, conventional snap fastener arrangements, clip arrangements and the like can be used. While the straps 13, 14 and 15 are preferably stiff so as to support the weight of the arm without stretching, this can be provided by a single thickness strip or a plurality of laminated layers. Strap materials can be cloth, plastic or the like. Other components of the device can be laminated or single thickness as desired. While three straps 13, 14 and 15 are preferred, more can be used in any desired positioning. Three straps are preferred in order to provide for proper rotational support and adjustment preferably with a front strap, back strap and midline strap.

In use of the arm support of this invention, the cylindrical humeral cuff which is to cover the upper arm is drawn over the upper arm into the position of FIG. 1. The cuff, of course, matches the contours of the upper arm due to the elastic band 51, and in some cases, the yieldability of the foam layer 50. Slippage is discouraged because of the high coefficient of friction of the foam layer or any covering material of the foam layer that may be used. The saddle is fixed in place by strap 16 and then the arm is positioned by mounting and adjustment of straps 13, 14 and 15. The band 17 is then positioned.

In some cases, the cuff can be initially sized specifically to a predetermined arm size. The cuff can have a closure such as VELCRO or fasteners rather than elastic band 17, so that it can be wrapped around the arm and formed into the cylindrical form shown. The use of the VELCRO attachment is preferred for the suspension straps so that the straps 13, 14 and 15 can be placed at any portion of the cuff that the fitter, or user, deems desirable and the angle between the straps and the saddle can be varied as desired. Asymmetrical tightening of the straps that is tightening the chest strap 13 and loosening the back strap 15, can act to rotate the arm inwardly. Conversely, if the back strap is tightened and the chest or forward strap is loosened, the arm rotates to the rear of the body with respect to the shoulder socket.

What is claimed:

1. An arm support for suspending the arm of the user below a user's shoulder joint, said support comprising:
   a shoulder saddle,
   an arm cuff having a high friction inner surface for contact with the arm of the user, and
   a plurality of adjustable straps extending between the shoulder saddle and the arm cuff for unloading the weight of the arm from the shoulder joint, said plurality of straps being pivotally attached to said shoulder saddle and permitting a large range of motion of said shoulder joint.

2. An arm support in accordance with claim 1 wherein said shoulder saddle comprises a stiff base portion and underlying body contacting padding portion.

3. An arm support in accordance with claim 2 and further comprising an encircling adjustable band holding said shoulder saddle against the weight of said arm cuff and the arm of the user in use.

4. An arm support in accordance with claim 3 and further comprising said plurality of straps comprising at least three straps which are adjustable with respect to their location on said arm cuff as well as for positioning the arm cuff with respect to distance from said shoulder saddle to allow adjustment as desired.

5. An arm cuff in accordance with claim 4 and further comprising said plurality of straps having hook and loop releasable attachment means for attachment to said arm cuff and a D shaped fastener for adjustment of said strap along its length.

6. An arm support in accordance with claim 1 and further comprising:
   said plurality of straps permitting a large range of motion of said shoulder joint, said straps having first means for permitting rotational movement of said cuff with respect to said shoulder saddle as well as positioning toward and away from said saddle upon placement of said straps so as to connect said saddle to said arm cuff,
   and separate means for movement and placement of said arm cuff with respect to said saddle.

7. An arm support in accordance with claim 1 and further comprising an encircling adjustable band holding said shoulder saddle against the weight of said arm cuff and the arm of the user in use.

8. In an arm support having a shoulder saddle and an arm cuff spaced from said saddle and constructed and arranged to surround and support the upper arm of a user, the improvement comprising
   a plurality of straps connected between said shoulder saddle and said arm cuff, each of said straps having first means for permitting rotational movement of said arm cuff with respect to said shoulder saddle upon adjustment of said straps as well as predetermined positioning toward and away from said saddle, and in addition, each of said straps having separate means for movement of said arm cuff towards and away from said saddle as desired with adjustment of said straps.

9. The improvement of claim 8 wherein said straps carry hook and loop releasable means acting as said first means and enabling varying points of engagement with said arm cuff both circumferentially and axially of said arm cuff.

10. The improvement of claim 9 and further comprising said cuff carrying a band for tightening said cuff about said arm.

11. The improvement of claim 9 wherein said cuff is resiliently deformable to closely conform to the arm of a user and said cuff has a high friction inner surface to engage said arm.

* * * * *